(12) United States Patent
Hsiao (10) Patent No.: US 11,421,850 B1
(45) Date of Patent: Aug. 23, 2022

(54) AROMA DIFFUSER WITH CHANGING OF ROTATING PATTERN LIGHTING

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Guangdong (CN)

( * ) Notice: Subject to any disclaimer, the term of this patent is extended or adjusted under 35 U.S.C. 154(b) by 0 days.

(21) Appl. No.: 17/580,476

(22) Filed: Jan. 20, 2022

(51) Int. Cl.
*F21V 1/10* (2006.01)
*A61L 9/03* (2006.01)
*F21V 9/45* (2018.01)
*F21V 33/00* (2006.01)

(52) U.S. Cl.
CPC .......... *F21V 1/10* (2013.01); *A61L 9/03* (2013.01); *F21V 9/45* (2018.02); *F21V 33/004* (2013.01); *A61L 2209/12* (2013.01)

(58) Field of Classification Search
CPC ... F21V 1/10; A61L 2209/12; A61L 9/03–037
See application file for complete search history.

(56) References Cited

U.S. PATENT DOCUMENTS

| | | | |
|---|---|---|---|
| 8,066,420 B2 | 11/2011 | Hsiao | |
| 8,147,097 B1 | 4/2012 | Hsiao | |
| 8,147,116 B1 | 4/2012 | Hsiao | |
| 8,201,957 B2 | 6/2012 | Hsiao | |
| 8,262,277 B2 | 9/2012 | Hsiao | |
| 8,783,907 B2 | 7/2014 | Hsiao | |
| 8,938,159 B2 | 1/2015 | Hsiao | |
| 8,974,107 B2 | 3/2015 | Hsiao | |
| 9,206,963 B2 | 12/2015 | Hsiao | |
| 9,395,061 B2 * | 7/2016 | Yang | F21S 6/001 |
| 2014/0307428 A1 * | 10/2014 | Ng | F21V 23/0457 362/202 |
| 2020/0121819 A1 * | 4/2020 | Lee | F21V 1/10 |

\* cited by examiner

Primary Examiner — Mariceli Santiago
(74) Attorney, Agent, or Firm — Sinorica LLC (57) ABSTRACT

An aroma diffuser with changing of rotating pattern lighting uses a patterned light-transmitting film designed to cover the outside of a light-emitting device, and one side of the patterned light-transmitting film is combined with a rotating ring driven by a transmission device. The light-emitting device radiates the light source to the patterned light-transmitting film, and the light effect of the pattern is transmitted to the outer light-transmitting casing through the patterned light-transmitting film to display the aesthetics of patterned light and shadow. The rotating ring can rotate the patterned light-transmitting film to change the lighting effect of its pattern or text. The light-emitting device can use different colors to generate light to reflect the graphics of the patterned light-transmitting film as colored light and shadow displayed in the light-transmitting casing, thereby producing light decoration or lighting and heating the aroma substances filled in the aroma diffuser.

10 Claims, 6 Drawing Sheets

AROMA DIFFUSER WITH CHANGING OF ROTATING PATTERN LIGHTING

BACKGROUND OF THE INVENTION

1. Field of the Invention

The present invention relates to scent releasing devices and more specifically, to an aroma diffuser with changing of rotating pattern lighting.

2. Description of the Related Art

Known light aroma diffusers, such as the light-emitting decoration or light-heated aroma diffusers of U.S. Pat. Nos. 8,783,907, 8,066,420, 8,262,277, 8,147,116, there is no light source to heat the aromatherapy substance at the same time. They cannot provide patterned lighting effects or mixed color lighting effects on the lampshade. These conventional aroma diffusers cannot be rotated and changed to continuously change the visual effect of the patterned light effects on the lampshade to generate better light effect and the atmosphere of the aromatic environment.

SUMMARY OF THE INVENTION

The present invention has been accomplished under the circumstances in view. It is therefore an object of the present invention to provide an aroma diffuser that provides changing of rotating pattern lighting.

The aroma diffuser with changing of rotating pattern lighting provided by the present invention comprises as light-transmitting casing, a container, a patterned light-transmitting film, a light-emitting device, a transmission device, a rotating ring, a power connection unit and a base. The light-transmitting casing comprises a first opening and a second opening. The first opening is formed on one side of the light-transmitting casing. The second opening is formed on the other side of the light-transmitting casing. The container is combined in the first opening of the light-transmitting casing. The base comprises a central through protrusion, a first hole and a second hole. The central through protrusion protrudes from the middle of the base. The first hole is defined in the central through protrusion. The second hole is adjacently opened on the side of the central through protrusion. The rotating ring has a third hole in the center. The third hole is rotatably arranged on the periphery of the central through protrusion. The power connection unit has the lower side thereof combined in the first hole of the base, and is used to electrically connected to a power supply. The light-emitting device is electrically connected to the upper side of the power connection unit. The patterned light-transmitting film is combined with the rotating ring on one side, and covers the outside of the light-emitting device. The transmission device comprises a linkage rod. The transmission device is combined in the base with the free end of the linkage rod passed through the second hole. The linkage rod is rotatably connected to one side of the rotating ring. The light-transmitting casing is combined above the base by the second opening side, and covers the rotating ring, the patterned light-transmitting film and the light-emitting device inside.

Thereby, the transmission device and the light-emitting device are combined with a power supply unit such as AC. The light-emitting device is used to emit light to heat the container. The container is used to place aromatic substances, such as solid fragrance, fragrant wax, essential oil or essential oil. The light-emitting device irradiates the container and conducts the heat source to the container to heat the aromatic substances to release the fragrance. Or fragrance capsules can be directly placed on the upper side of the container and directly heated to release the fragrance. In one embodiment, the fragrance substance is a fragrant wax. The transmission device and its linkage rod rotate and drive the rotating ring and the patterned light-transmitting film to rotate. The patterned light-transmitting film can make or print various patterns, textures, characters, or various hollow patterns. The light of the light-emitting device illuminates the pattern of the patterned light-transmitting film, to develop or produce totem light and shadow effect or text projection, and conduct outward to the light-transmitting casing, and at the same time, the image of the rotating patterns or text of the rotating patterned light-transmitting film produces vivid projected light effects shown in the light-transmitting casing.

The light-emitting device can provide various colors of light radiating on the pattern of the patterned light-transmitting film, and emit omnidirectional light colors and transmit the pattern of the patterned light-transmitting film to the light-transmitting casing. The rotating device drives and rotates the patterned light-transmitting film, so as to generate ambient lighting decoration or lighting effects such as patterns or characters that are constantly rotating and changing, and match the aroma atmosphere, which is different from the conventional lighting aroma diffusers.

DETAILED DESCRIPTION OF THE PREFERRED EMBODIMENT

Figure 1:
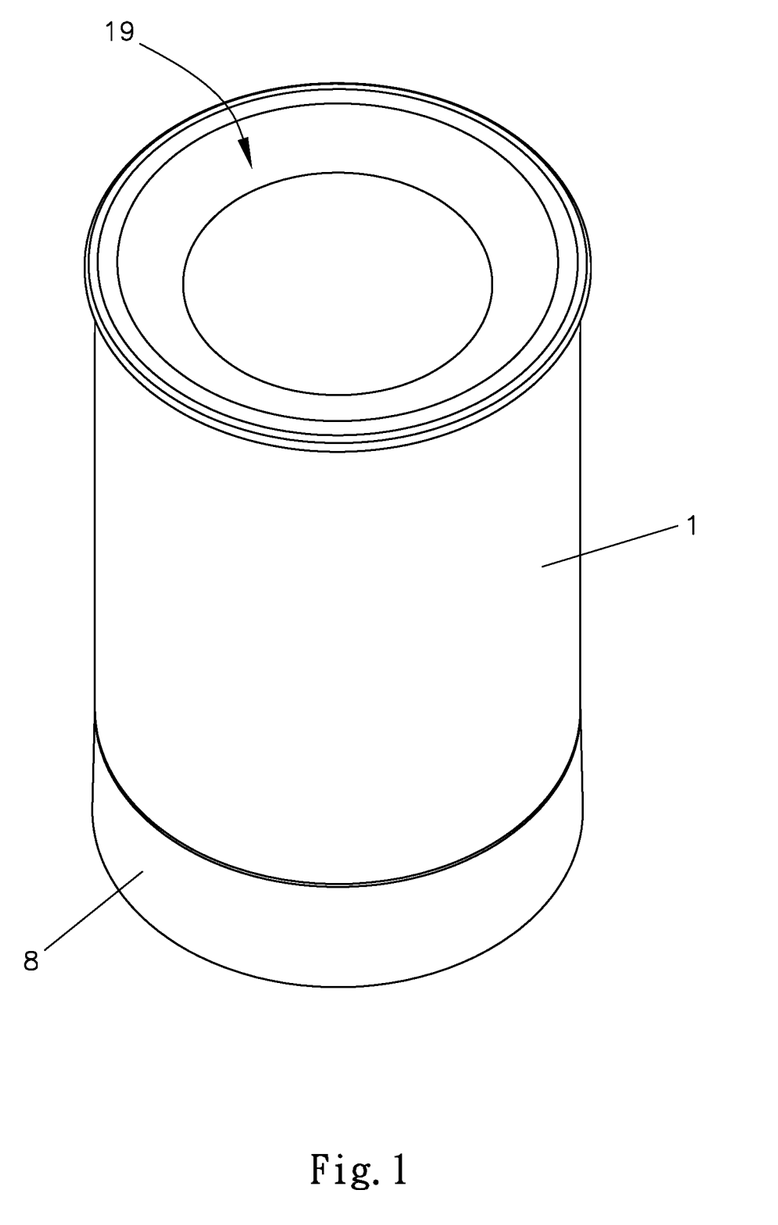
FIG. 1 is an elevational view of an aroma diffuser with changing of rotating pattern lighting in accordance with the present invention.
Figure 2:
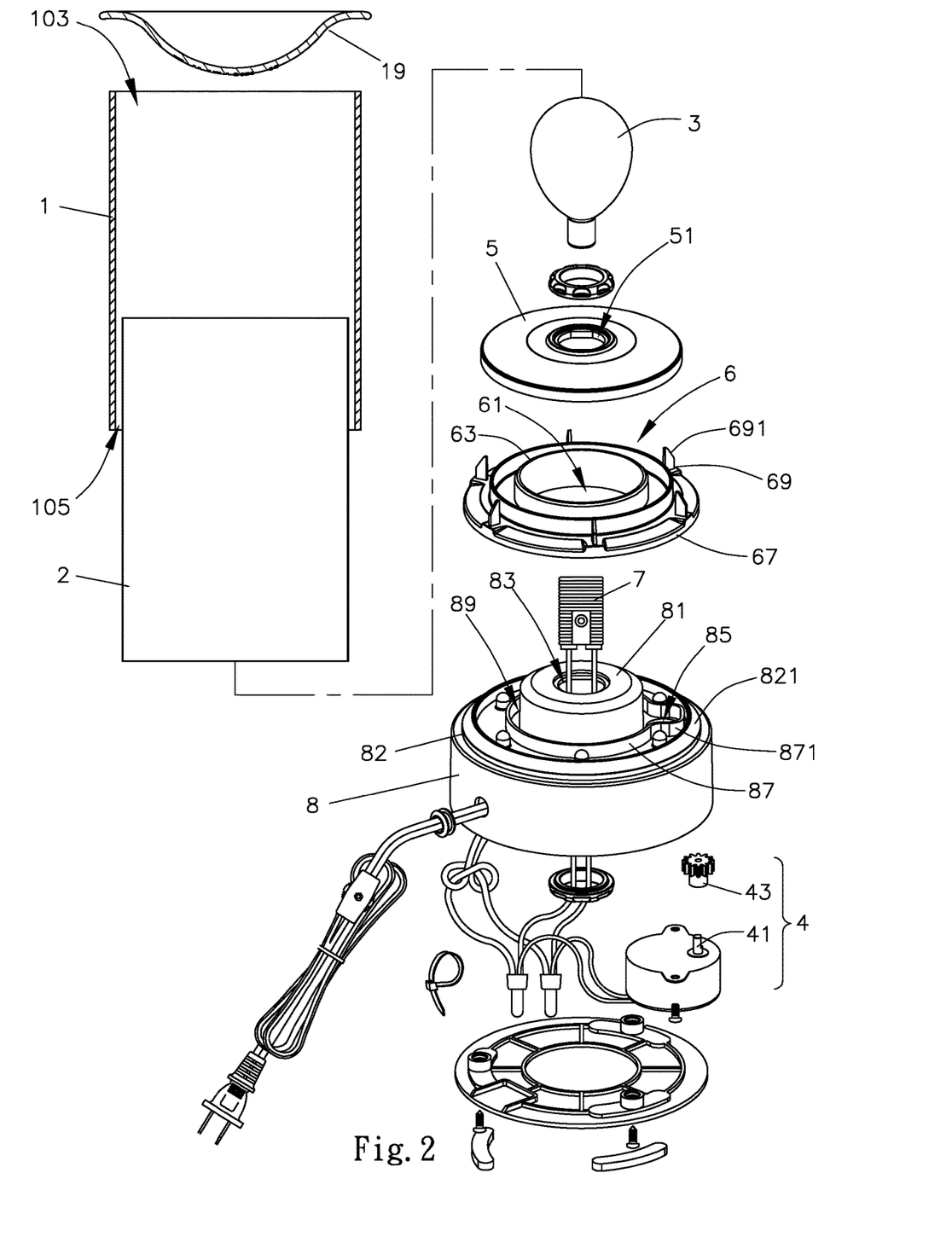
FIG. 2 is an exploded view of the aroma diffuser with changing of rotating pattern lighting in accordance with the present invention.
Figure 3:
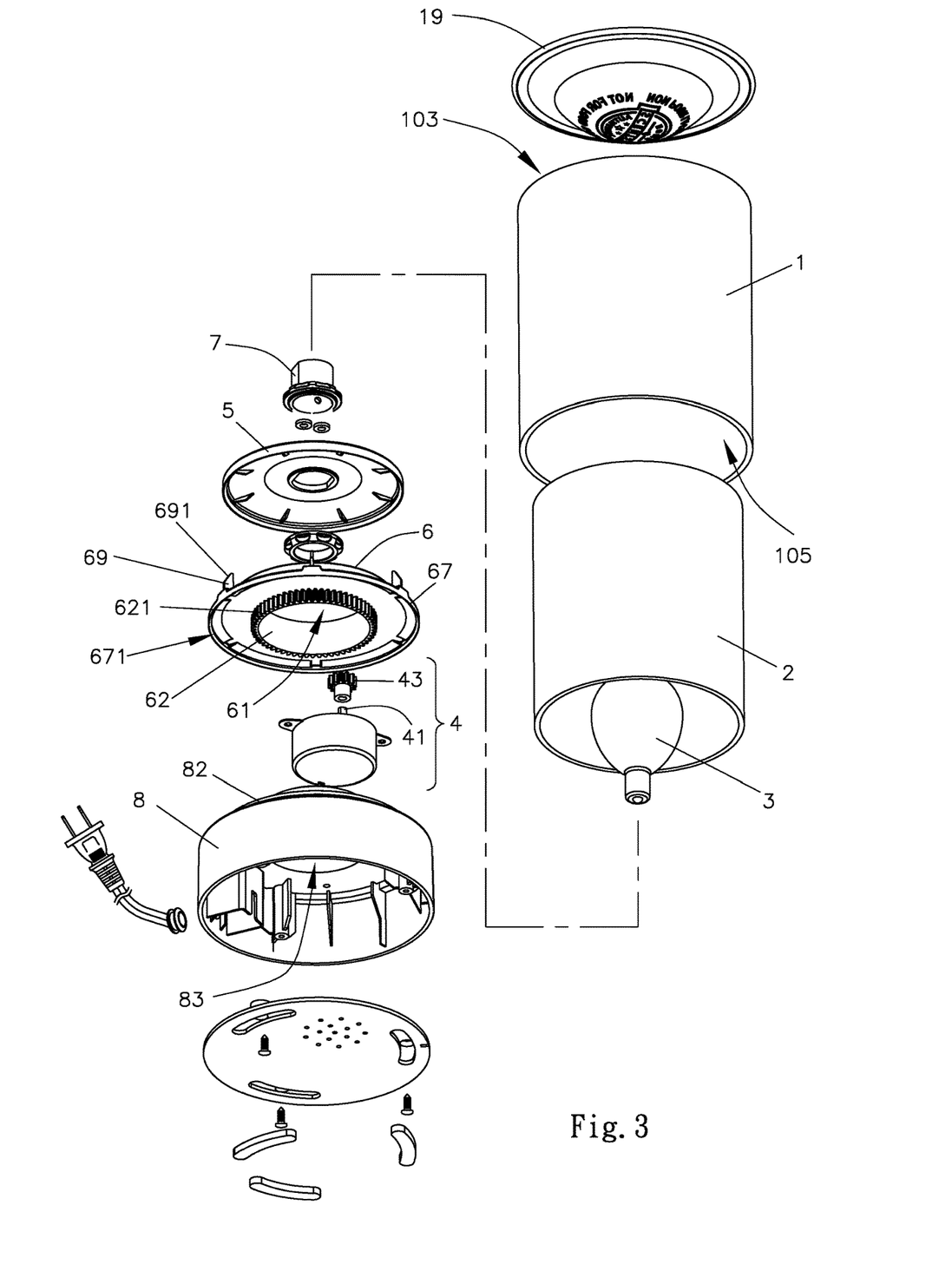
FIG. 3 corresponds to FIG. 2 when viewed from another angle.
Figure 4:
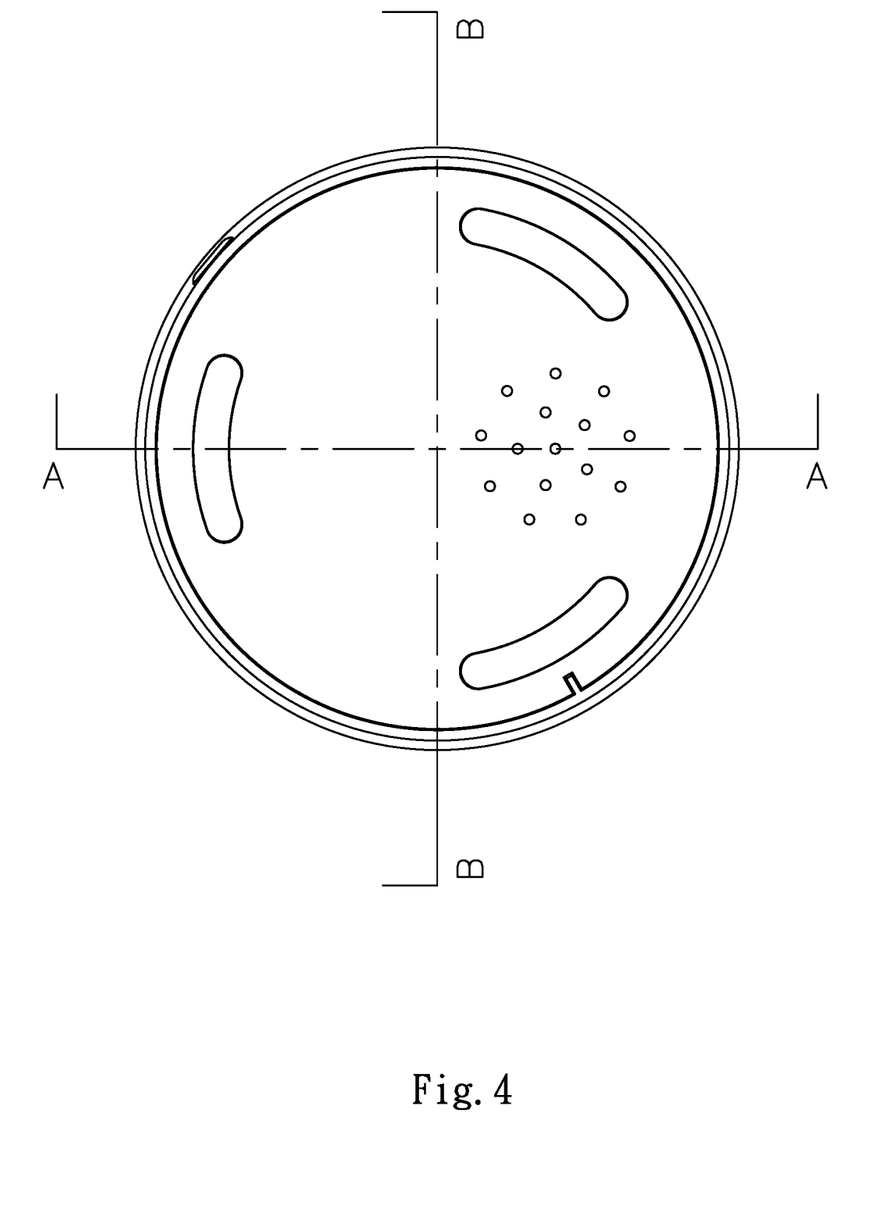
FIG. 4 is a bottom view of the aroma diffuser with changing of rotating pattern lighting in accordance with the present invention.

Referring to FIGS. 1-4, an aroma diffuser with changing of rotating pattern lighting in accordance with the present invention is shown. The aroma diffuser comprises a light-transmitting casing 1, a container 19, a patterned light-transmitting film 2, a light-emitting device 3, a transmission device 4, a rotating ring 6, a power connection unit 7, and a base 8. The light-transmitting casing 1 comprises a first opening 103 and a second opening 105. The first opening 103 is formed on one side of the light-transmitting casing 1. The second opening 105 is formed on the other side of the light-transmitting casing 1. The container 19 is incorporated in the first opening 103 of the light-transmitting casing 1. The base 8 comprises a central through protrusion 81 in communication with the inside of the base 8, a first hole 83, and a second hole 85. The central through protrusion 81 protrudes from the middle of the base 8, and the first hole 83 is formed in the central through protrusion 81. The second hole 85 is adjacently opened on one side of the central through protrusion 81. There is a third hole 61 in the center of the rotating ring 6, and the third hole 61 is rotatably penetrated in the periphery of the central through protrusion 81. The lower side of the power connection unit 7 is combined in the first hole 83 of the base 8 for electrically connecting a power source. The light-emitting device 3 is electrically connected to the upper side of the power connection unit 7. One side of the patterned light-transmitting film 2 is combined with the rotating ring 6, while the outer side of the light-emitting device 3 is masked. The transmission device 4 comprises a linkage rod 41. The transmission device 4 is combined in the base 8 and the free end of the linkage rod 41 passes through the second hole 85, and the linkage rod 41 is rotatably connected to one side of the rotating ring 6. The light-transmitting casing 1 is combined on the top of the base 8 by the second opening 105, and simultaneously covers this rotating ring 6, the patterned light-transmitting film 2 and the light-emitting device 3.

Thereby, the transmission device 4 and the light-emitting device 3 are combined with a power supply unit such as AC. The light-emitting device 3 is used to emit light to heat this container 19, and the container 19 is used to place aromatic substances, such as solid aromatic substances, fragrant wax, essential oils or essential oils. The light-emitting device 3 irradiates the container 19 and conducts the heat source to the container 19 to heat the aromatic substance and release the fragrance. In the embodiment, the aromatic material is fragrant wax. The container 19 is a translucent container, made of materials such as glass, acrylic, translucent plastic or silicone. The transmission device 4 and its linkage rod 41 rotate and drive the rotating ring 6 and the patterned light-transmitting film 2 to rotate. The patterned light-transmitting film 2 can make or print various patterns, textures, characters, or various hollow patterns. The light of the light-emitting device 3 illuminates the pattern of the patterned light-transmitting film 2, to develop or produce totem light and shadow effect or text projection, and conduct outward to the light-transmitting casing 1, and at the same time, the image of the rotating patterns or text of the rotating patterned light-transmitting film 2 produces vivid projected light effects shown in the light-transmitting casing 1.

The light-emitting device 3 can provide various colors of light radiating on the pattern of the patterned light-transmitting film 2, and emit omnidirectional light colors and transmit the pattern of the patterned light-transmitting film 2 to the light-transmitting casing 1. The rotating device 4 drives and rotates the patterned light-transmitting film 2, so as to generate ambient lighting decoration or lighting effects such as patterns or characters that are constantly rotating and changing, and match the aroma atmosphere, which is different from the conventional lighting aroma diffusers.

This power connection unit 7 comprises, for example, a lamp holder, a power circuit board or various PCB boards to connect various light-emitting devices, and an external power supply such as AC or an internal power supply to provide power to the light-emitting device 3 to emit light and generate heat sources. The light-emitting device 3 includes but is not limited to colored light bulbs, various light bulbs or LEDs. In the embodiment, it is a light bulb or a colored light bulb electrically connected to the lamp holder of the power connection unit 7 to emit light radiation heat source in all directions to illuminate the container 19, and the light of the light source illuminates the pattern of the patterned light-transmitting film 2 at the same time to produce totem light and shadow effects.

Figure 5:
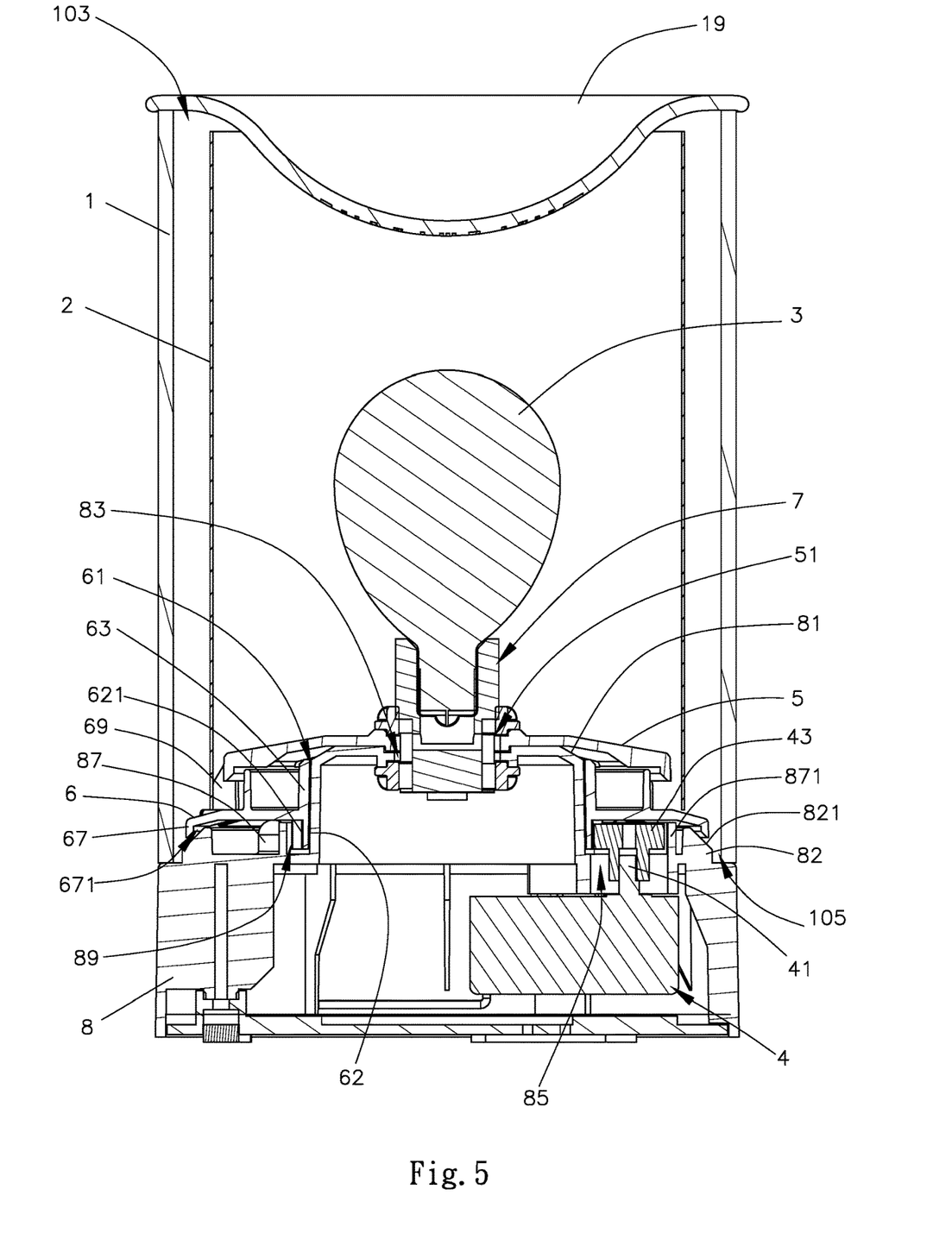
FIG. 5 is a sectional view taken along line A-A of FIG. 4.

Referring to FIGS. 2-5, it is an embodiment of the aroma diffuser with changing of rotating pattern lighting of the present invention. The rotating ring 6 comprises a lower ring portion 62 protruding downward from the outer periphery of the lower side of the third hole 61. When the third hole 61 of the rotating ring 6 passes through the central through protrusion 81, the lower ring portion 62 is rotatably sleeved on the lower periphery of the central through protrusion 81 at the same time. The rotating ring 6 is rotatably sleeved on the lower side of the central through protrusion 81 by the increased area of the inner side wall of the lower ring portion 62, so as to increase the contacting and rotating area of the rotating ring 6 and the central through protrusion 81. It can improve the stability of the rotating ring 6 in the periphery of the central through protrusion 81, and at the same time can improve the stability of the patterned light-transmitting film 2 connected to the rotating ring 6 when it rotates, and prevent the patterned light-transmitting film 2 from shaking.

Referring to FIGS. 2 to 5, it is an embodiment of the aroma diffuser with changing of rotating pattern lighting of the present invention, further comprising a tooth pattern 621 formed around the lower ring portion 62. The transmission device 4 further comprises a gear 43. The diameter of the lower ring portion 62 may be larger than the diameter of the gear 43 in the embodiment. The number of teeth of the tooth pattern 621 around the lower ring portion 62 may be more than the number of teeth of the gear 43 in the embodiment. The gear 43 and the tooth pattern 621 of the lower ring portion 62 are in engagement with each other. The gear 43 is combined with the free end of the linkage rod 41 of the transmission device 4, whereby the transmission device 4 and the linkage rod 41 rotate to drive the gear 43, which drives the tooth pattern 621 to rotate the lower ring portion 62 and the entire rotating ring 6 to rotate. Through the gear 43 and the tooth pattern 621 with different gear ratios, the rotational speed of the transmission can be reduced to a fixed value, and the torque can be transmitted to the rotating ring 6, so that the rotating ring 6 rotates at a certain speed, and the patterned light-transmitting film 2 and the rotating ring 6 rotate together. The patterned light-transmitting film 2 and its patterns can be seen through the transparent external light-transmitting casing 1, which is made of, for example, glass or plastic, and the light-transmitting pattern can show the effect of rotating lights.

Figure 6:
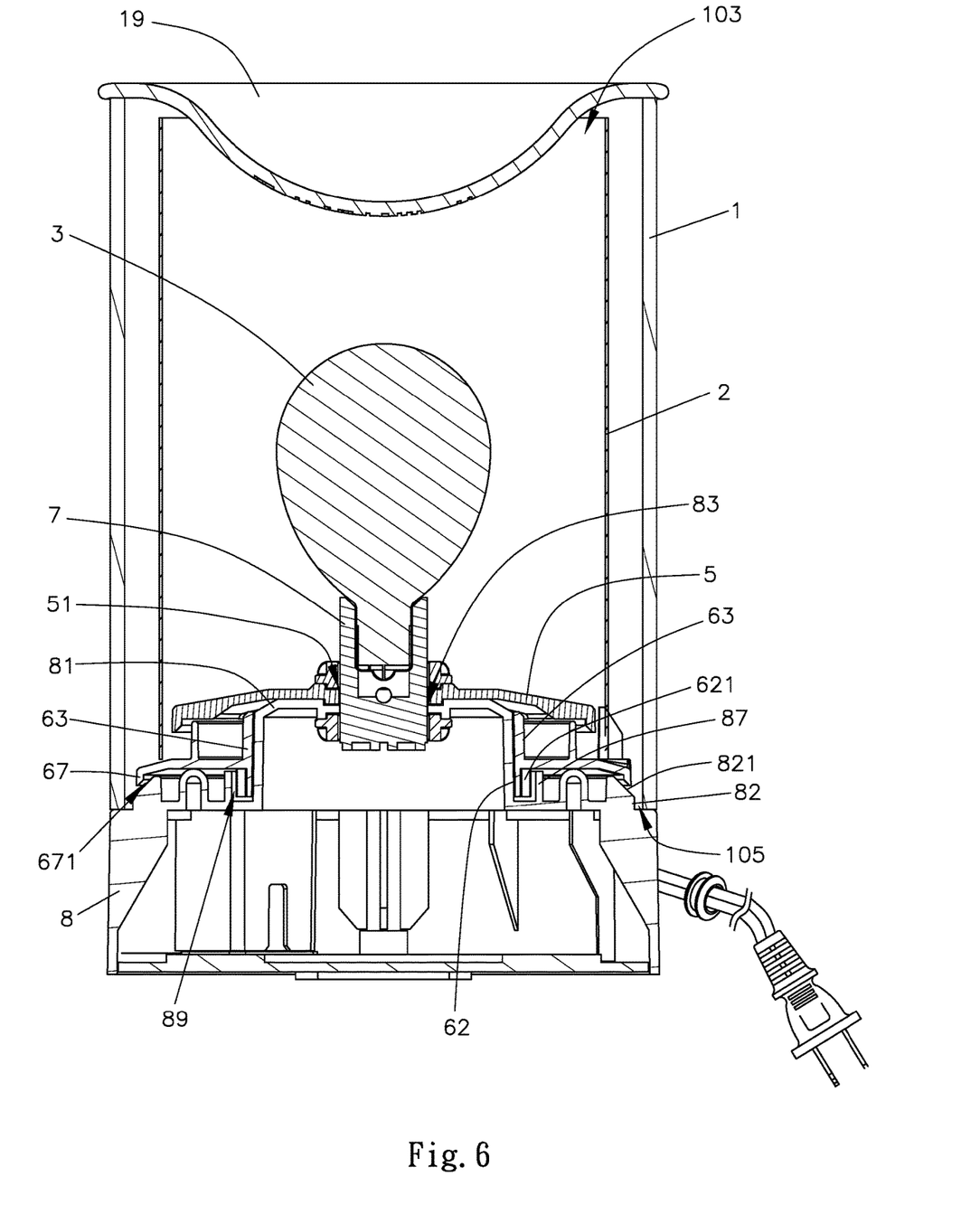
FIG. 6 is a sectional view taken along line B-B of FIG. 4.

Referring to FIGS. 2 to 6, it is an embodiment of the aroma diffuser with changing of rotating pattern lighting of the present invention. The base 8 comprises a protrusion 87, which protrudes from the surface of the base 8 and surrounds the central through protrusion 81, the gear 43 and the outside of the second hole 85. The height of the protrusion 87 is lower than the central through protrusion 81. A first groove 89 is formed between the protrusion 87 and the periphery of the central through protrusion 81. The lower ring portion 62 is located within the first groove 89. The rotating ring 6 and its lower ring portion 62 and the gear 43 rotate, and the first groove 89 can constrain and protect the lower ring portion 62 and the gear 43 in a stable rotational process. In the embodiment, the rotating ring 6 and its lower ring portion 62 and the gear 43 rotate, and long-term use may cause gap displacement due to vibration and wear in the later life cycle of the product. The first groove 89 and the extrusion 87 constrain and guide the lower ring portion 62 and the rotating ring 6 driven by the gear 43 to maintain stability.

Referring to FIGS. 2-5, it is an embodiment of the aroma diffuser with changing of rotating pattern lighting of the present invention. The protrusion 87 comprises a protruding portion 871 formed on one side of the protrusion 87. The protruding portion 871 extends around the second hole 85 and the periphery of the gear 43, and has a structure similar to the shape of the hand of a table tennis racket. The protrusion of the protruding portion 871 allows the diameter of the protrusion 87 to be restricted to a small extent, so that the diameter of the first groove 89 formed by the protrusion 87 surrounding the central through protrusion 81 can be reduced to be close to the lower ring portion 62 or the diameter is slightly larger than the lower ring portion 62, so that the first groove 89 and the protrusion 87 can be formed on the narrow inner side of the diffuser without taking up too much space.

Referring to FIGS. 2-5, it is an embodiment of the aroma diffuser with changing of rotating pattern lighting of the present invention. The base 8 further comprises an annular rail 82, which protrudes from the surface of the base 8 and surrounds the central through protrusion 81, the second hole 85 and the outside of the protrusion 87. The peripheral end 67 of the rotating ring 6 rotatably contacts the annular rail 82. When the rotating ring 6 rotates with the central through protrusion 81 as the center, the peripheral end 67 is in contact with the surface of the annual rail 82 to slide, and the horizontal rotation of the rotating ring 6 can be relatively stable.

Referring to FIGS. 2 to 6, it is an embodiment of the aroma diffuser with changing of rotating pattern lighting of the present invention. The peripheral end 67 of the rotating ring 6 is formed with a first inclined surface 671. The upper side of the annual rail 82 is formed with a second inclined surface 821. The first inclined surface 671 of the peripheral end 67 of the rotating ring 6 rotates in contact with the second inclined surface 821 of the annular rail 82, and the sliding can be smoother. At the same time, the sliding instability that may be generated due to the difference in contact surface expansion and contraction during the rotation of the peripheral end 67 and rubbing between the peripheral end 67 and the second inclined surface 821 can be overcome by the sliding surface structure. In this way, The horizontal rotation of the rotating ring 6 can maintain stability and is not easy to shake.

Referring to FIGS. 2 to 6, it is an embodiment of the aroma diffuser with changing of rotating pattern lighting of the present invention. An upper ring portion 63 protrudes upward from the outer periphery of the upper side of the third hole 61 of the rotating ring 6. The upper ring portion 63 is rotatably sleeved on the lower periphery of the central through protrusion 81. The rotating ring 6 is rotatably sleeved on the upper side of the central through protrusion 81 by the increased area of the inner wall surface of the upper ring portion 63, so as to increase the contacting and rotating area of the rotating ring 6 and the central through protrusion 81. Further, the rotation of the rotating ring 6 at the periphery of the central through protrusion 81 is more stable, and at the same time, the stability of the patterned light-transmitting film 2 connected to the rotating ring 6 can be improved when rotating, and the patterned light-transmitting film 2 can be prevented from shaking.

Referring to FIGS. 2-5, it is an embodiment of the aroma diffuser with changing of rotating pattern lighting of the present invention. The rotating ring 6 comprises a plurality of fixing posts 69, and a third inclined surface 691 is formed on the upper side of each fixing post 69. The plurality of fixing posts 69 are arranged on the periphery of the upper side of the rotating ring 6 at intervals. The patterned light-transmitting film 2 is a hollow cylindrical structure, and the inner wall on the lower side of the hollow cylindrical in the patterned light-transmitting film 2 is sleeved on the outside of the fixing posts 69. The third inclined surfaces 691 allow the inner wall of the lower side of the hollow cylindrical structure of the patterned light-transmitting film 2 to be nested or pulled away from the outer side of the fixing posts 69 more smoothly and easily.

Referring to FIGS. 2 to 6, it is an embodiment of the aroma diffuser with changing of rotating pattern lighting of the present invention. The aroma diffuser further comprises a top cover 5. The top cover 5 is provided with a fourth hole 51. The top cover 5 is combined on the upper side of the base 8, the fourth hole 51 corresponds to the first hole 83, and the power connection unit 7 is combined in the fourth hole 51. The top cover 5 is located on the inner side of the patterned light-transmitting film 2 at the same time, and the top cover 5 shields or protects the lower rotating ring 6 and the gear 43 or the motor 4 and other components. At the same time, the top cover 5 prevents the light and heat source generated by the light-emitting device 3 from penetrating and dissipating downward, or the heat source affecting the operation efficiency of the rotating ring 6, the gear 43 or the motor 4 and other components.

The above are only multiple embodiments of the present invention, and cannot be used to limit the scope of implementation of the present invention, that is, all simple equivalent changes and modifications made according to the claims of the present invention and the specification should still belong to the scope of protection of the present invention.

What the invention claimed is:

1. An aroma diffuser with changing of rotating pattern lighting, comprising: a light-transmitting casing, a container, a patterned light-transmitting film, a light-emitting device, a transmission device, a rotating ring, a power connection unit, and a base, wherein:

said light-transmitting casing comprises a first opening formed on one side thereof and a second opening formed on an opposite side thereof;

said container is combined in said first opening of said light-transmitting casing;

said base comprises a central through protrusion in communication with the inside of said base, a first hole and a second hole, said central through protrusion protruding from the middle of said base, said first hole being formed in said central through protrusion, said second hole being adjacently opened on one side of said central through protrusion;

said rotating ring comprises a third hole in the center, said third hole being rotatably penetrated in the periphery of said central through protrusion;

said power connection unit is combined in said base to electrically connect a power source;

said light-emitting device is electrically connected to said power connection unit;

said patterned light-transmitting film is combined with said rotating ring on one side, and covers the outside of said light-emitting device;

said transmission device comprises a linkage rod, said transmission device being combined in said base, said linkage rod having the free end passed through said second hole, said linkage rod being rotatably connected to one side of said rotating ring; and said light-transmitting casing is combined above said base by said second opening side, and covers said rotating ring, said patterned light-transmitting film and said light-emitting device inside.

2. The aroma diffuser with changing of rotating pattern lighting as claimed in claim 1, wherein said rotating ring comprises a lower ring portion protruding downward from a lower side thereof and rotatably sleeved on a lower periphery of said central through protrusion.

3. The aroma diffuser with changing of rotating pattern lighting as claimed in claim 2, wherein said rotating ring further comprises a tooth pattern formed around said lower ring portion, said transmission device further comprises a gear combined with the free end of said linkage rod of said transmission device and meshed with said tooth pattern of said lower ring portion.

4. The aroma diffuser with changing of rotating pattern lighting as claimed in claim 3, wherein said base further comprises a protrusion, said protrusion protruding from the surface of said base and surrounding said central through protrusion, said gear and said second hole, the height of said protrusion being lower than said central through protrusion, said protrusion and said central through protrusion defining a first groove therebetween for the placement of said lower ring portion.

5. The aroma diffuser with changing of rotating pattern lighting as claimed in claim 4, wherein said protrusion comprises a protruding portion located on one side thereof, said protruding portion extending around the periphery of said second hole and said gear.

6. The aroma diffuser with changing of rotating pattern lighting as claimed in claim 5, wherein said base comprises an annular rail, said annular rail protruding from the surface of said base and surrounding said central through protrusion, said second hole and said protrusion, said rotating ring comprising a peripheral end, said peripheral end rotatably contacting said annular rail when said rotating ring rotates on said central through protrusion.

7. The aroma diffuser with changing of rotating pattern lighting as claimed in claim 6, wherein said peripheral end of said rotating ring is provided with a first inclined surface, said annular rail comprises a second inclined surface, and said first inclined surface of said rotating ring peripheral end is rotatably contacting said second inclined surface of said annular rail.

8. The aroma diffuser with changing of rotating pattern lighting as claimed in claim 1, wherein said rotating ring comprises an upper ring portion protruding upward from the outer periphery of an upper side of said third hole and rotatably sleeved on a lower periphery of the central through protrusion.

9. The aroma diffuser with changing of rotating pattern lighting as claimed in claim 1, wherein said rotating ring comprises a plurality of fixing posts, each said fixing post having a third inclined surface formed on a top side thereof, said fixing posts being set at intervals on the periphery of an upper side of said rotating ring, said patterned light-transmitting film is a hollow cylindrical structure sleeved on the outside of said fixing posts.

10. The aroma diffuser with changing of rotating pattern lighting as claimed in claim 1, further comprising a top cover located on the inside of said patterned light-transmitting film, said top cover being provided with a fourth hole, said top cover being combined on an upper side of said base, said fourth hole corresponding to said first hole and holding said power connection unit therein.

\* \* \* \* \*